United States Patent [19]

Chiodini et al.

[11] Patent Number: 4,895,836
[45] Date of Patent: Jan. 23, 1990

[54] NOR-CHOLANIC ACID DERIVATIVES, A PROCESS FOR THEIR PREPARATION, THEIR USE AND PHARMACEUTICAL COMPOSITIONS CONTAINING THEM

[75] Inventors: Laura Chiodini, Busto Arsizio; Mauro Gobbini, Sesto Calende; Sergio Mantegani, Milan; Daniel Ruggieri, Milan; Aldemio Temperilli, Milan; Gabriella Traquandi, Cornate d'Adda; Patrizia Ferrari, Varese, all of Italy

[73] Assignee: Farmitalia Carlo Erba S.p.A., Milan, Italy

[21] Appl. No.: 133,043

[22] PCT Filed: Jan. 7, 1987

[86] PCT No.: PCT/EP87/00006
§ 371 Date: Oct. 29, 1987
§ 102(e) Date: Oct. 29, 1987

[87] PCT Pub. No.: WO87/04166
PCT Pub. Date: Jul. 16, 1987

[30] Foreign Application Priority Data

Jan. 9, 1986 [GB] United Kingdom ............... 8600491

[51] Int. Cl.⁴ .................. C07J 00/00; C07H 15/24; A61K 31/58
[52] U.S. Cl. .................. 514/26; 514/182; 536/5; 536/6; 536/6.7; 540/90
[58] Field of Search ........... 536/5, 6, 6.1; 514/182, 514/26, 172; 260/397.5; 540/90

[56] References Cited

U.S. PATENT DOCUMENTS 4,088,757  5/1978  Peterson .................. 536/5

FOREIGN PATENT DOCUMENTS 1903901  9/1970  Fed. Rep. of Germany .
2205331  5/1974  France .
2339623  8/1977  France .

Primary Examiner—H. M. S. Sneed
Assistant Examiner—J. Saba
Attorney, Agent, or Firm—Brooks Haidt Haffner & Delahunty

[57] ABSTRACT

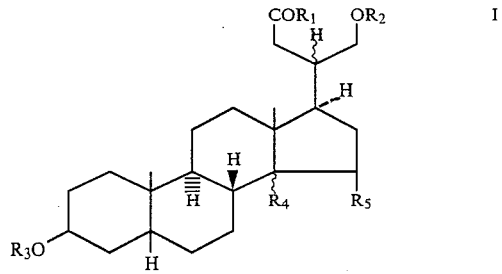

Compounds I (either $R_1 = OH$, $C_1-C_4$ alkoxy and $R_2 = H$, $C_1-C_4$ alkyl, or $R_1 + R_2 =$ a chemical bond; $R_3 =$ an aminodeoxy or aminodideoxy or aminotrideoxy sugar residue of the D and L series, the glycosidic linkage being $\alpha$ or $\beta$: and either $R_4 = OH$ and $R_5 = H$ or $R_4 + R_5 =$ a chemical bond) and their pharmaceutically acceptable salts are useful as antihypertensive agents. Their preparation and use as well as pharmaceutical compositions containing them are also described.

6 Claims, No Drawings

NOR-CHOLANIC ACID DERIVATIVES, A PROCESS FOR THEIR PREPARATION, THEIR USE AND PHARMACEUTICAL COMPOSITIONS CONTAINING THEM

The invention provides aminoglycoside steroids having the general formula I

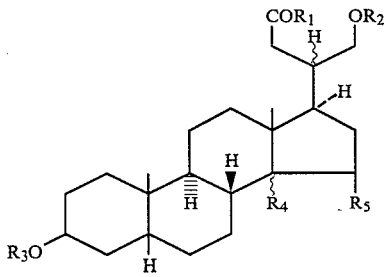

wherein either $R_1$ represents a hydroxy group or an alkoxy group having from 1 to 4 carbon atoms and $R_2$ represents a hydrogen atom or an alkyl group having from 1 to 4 carbon atoms, or $R_1$ and $R_2$ taken together represent a chemical bond; $R_3$ represents an optionally alkyl-substituted aminodeoxy or aminodideoxy or aminotrideoxy sugar residue of the D or L series; and either $R_4$ represents a hydroxy group and $R_5$ represents a hydrogen atom or $R_4$ and $R_5$ taken together represent a chemical bond. Such sugar residues are, for example, 2-amino or 2-alkylamino-2-deoxy-hexopyranosyl, 3-amino or 3-alkylamino-3-deoxy-hexopyranosyl, 3-amino or 3-alkylamino-3,6-dideoxy-hexopyranosyl, 3-amino or 3-alkyl-amino-2,3,6-trideoxy-hexopyranosyl and 4-amino or 4-alkylamino-2,4,6-trideoxy-hexopyranosyl residues of the D and L series. The optional alkyl substituents of the sugar residue are preferably lower alkyl with $C_1$-$C_4$ atoms, e.g. methyl, ethyl, propyl and butyl. Advantageously the alkyl radicals may substitute the amino group of the sugar residue.

The wavy lines in the formulae indicate that the hydrogen atom or the substituent may be above or under the plane of the ring system providing optically active isomer forms having different absolute configurations. These optically active forms either in the form of the racemate or as pure optical antipodes are encompassed by this invention. The racemates can be separated in accordance with methods known per se. Preferably the racemic mixture is reacted with an optically active separating agent to form diastereomers. As separating agents e.g. optically active acids such as the D- and L-form of tartaric acid, diacetyl-tartaric acid, dibenzoyl-tartaric acid, mandelic acid, malic acid, lactic acid or the various optically active camphersulfonic acids like β-camphersulfonic acid may be mentioned.

Of course it is also possible to obtain optically active compounds of formula I in utilizing starting materials being optically active.

The glycosidic linkage can be α or β. An alkoxy group may be methoxy, ethoxy, propoxy or butoxy group, an alkyl group may be methyl, ethyl, propyl or butyl group.

Pharmaceutically acceptable salts of these aminoglycoside steroids are included in the invention.

"Pharmaceutically acceptable salts" refers to those salts which retain the biological effectiveness and properties of the free basis and which are not biologically or otherwise undesirable. Such salts are formed with inorganic acids such as hydrochloric, hydrobromic, sulfuric, nitric or phosphoric acid and organic acids such as acetic, propionic, glycolic, pyruvic, oxalic, malic, malonic, succinic, maleic, fumaric, tartaric, citric, benzoic, cinnamic, mandelic, methanesulfonic, ethanesulfonic, p-toluene sulfonic or salicylic acid.

The invention further provides a process for the preparation of the aminoglycoside steroids of the general formula I as herein defined, which process comprises condensing a nor-cholane derivative having the general formula II

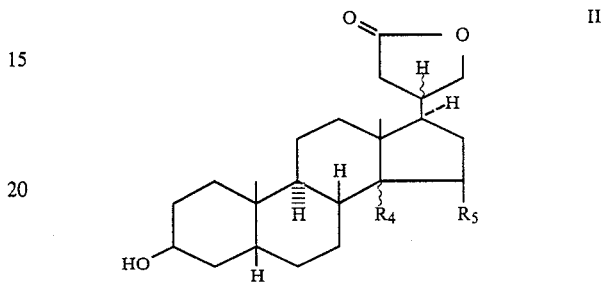

wherein $R_4$ and $R_5$ have the above meanings with a protected 1-halo derivative of an optionally alkyl substituted aminodeoxy, aminodideoxy or aminotrideoxy sugar of the D or L series and removing the protecting groups from the resultant compound. The removal of the protecting group is advantageously obtained with a base.

The condensation is desirably carried out in a suitable organic solvent, such as chloroform, methylene dichloride, benzene, toluene, acetonitrile or nitromethane, in the presence of a catalyst. The catalyst may preferably by silver oxide or carbonate or trifluoromethanesulphonate, Fetizon's reagent, mercuric cyanide or bromide. In the process it may be desirable to use drierite or a molecular sieve as drying agents or the azeotropic distillation method during reaction, at a temperature of $-5°$ C. to $100°$ C. The reaction time may vary broadly and often be from one to eight hours.

The base used to remove the protecting groups may be a hydroxide or methoxide of sodium or potassium or barium or may be triethylamine and the reaction may be performed at room temperature over a period of sore hours to several days.

This operation generally gives compounds of the general formula I wherein $R_1$ is hydroxy or alkoxy group and $R_2$ is a hydrogen atom or alkyl group. These compounds may be converted by cyclization into the other compounds of the general formula I wherein $R_1$ and $R_2$ together represent a chemical bond, forming a lactone ring. The cyclization may be carried out in hydrochloric acid at room temperature and pH 1-2 for from three to five hours.

The nor-cholane derivatives of the formula II and the aminodeoxy, aminodideoxy and aminotrideoxy sugars, possibly in alkylated form respectively, used a starting materials are well known compounds or they may be prepared by procedures familiar to those skilled in the art.

The aminoglycoside nor-cholanic acid derivatives according to the invention and their pharmaceutically acceptable salts are capable of inhibiting specific ouabain binding without inhibiting $Na^+$, $K^+$-ATPase activity and thus they may form useful pharmaceutical compositions, particularly for the treatment of hypertension. Thus the inventive compounds may also be used for the making of medicaments effective against hypertension.

'In vitro' assays to test the ability of aminoglycoside steroids of formula I to displace specific ouabain binding to the (Na+-K+)-ATPase receptors without inhibiting the (Na+-K+)-ATPase enzymatic activity.

Radiochemical assay

A microsomial fraction enriched in (Na+-K+)-ATPase was prepared from dog kidney outer medulla, according to Jørgensen (BBA 356: 36–52, 1974).

The partially purified enzyme (0.5 μg of protein) was incubated in 3 mM $MgCl_2$, 3 mM EGTA, 80 mM Hepes buffer (pH 7.4) and 2 mM $y^2$-$P^{32}$-ATP, final volume 110 μl, at 37° C. for 15 minutes with increasing concentrations of ouabain (as reference compound) or aminoglycoside steroids.

The reaction was stopped by the addition of 0.1 mM of cold perchloric acid (10% final concentration) and 0.5 ml of charcoal suspension (20% w/v). The suspension was centrifuged and the content of $^{32}P$ in the supernatant was measured by liquid scintillation counting. (ref. Mall F. et al.; Biochem. Pharm. 33: N.1, 47–53, 1984).

The effects of various concentrations of aminoglycoside steroids and ouabain were expressed as a percentage of inhibition of the total (Na+-K+)-ATPase activity and $IC_{50}$ values were calculated. The compounds of the formula I are inactive in this test.

Displacement of ouabain ($H^3$) binding from human red blood cells

The procedure has been described elsewhere (Erdmann E. et al.; Arzneim. Forsh 34(II), no. 10: 1314, 1984).

Washed erythrocytes (about $1-1.8 \times 10^9$/ml) were incubated in 130 mM NaCl, 1 mM $MgCl_2$, 10 mM glucose, 10 mM sucrose, 10 mM Tris/HCl buffer (pH 7.4) $2 \times 10^{-9}$M $^3H$ ouabain and increasing concentration of the unlabelled aminoglycoside steroids, at 37° C. for 5 hours. Bound ouabain was quantitated by a rapid filtration technique (Whatman GF/C glass filter membranes; 'Whatman' is a Trade Mark) to separate free from membrane-bound ouabain. The radioactivity in the filters was determined by liquid scintillation counting. Non specific binding was defined as the binding in the presence of $10^{-3}$M unlabelled ouabain.

This dissociation constant ($K_D$ value) was calculated from the concentration of unlabelled aminoglycoside steroids which inhibit $^3H$-ouabain binding by 50% at equilibrium, by the method of Erdmann et al. (Schmiedeberg's Arch. Pharmacol. 283: 335, 1973). The compounds of the formula I are effective in this test with a $K_D$ value range of from $10^{-9}$ to $10^{-6}$.

Inhibition of Na+ efflux mediated by the (Na+-K+)-ATPase in human red blood cells The procedure has been described elsewhere (Garay et al. Biochem. Pharmacol. 33:2013–2020, 1984). Washed red blood cells were suspended to a hematocrit of 20–25% in 74 mM $MgCl_2$, 2 mM KCl, 84 mM sucrose, 10 mM MOPS/Tris buffer (pH 7.4 at 37° C.) and 10 mM glucose.

Red cell suspensions were added in the cold to tubes containing $Mg^{++}$ sucrose-$K^+$ medium with increasing concentration of ouabain and fixed concentrations of aminoglycoside steroids. The tubes were incubated at 37° C. and aliquots of the suspensions were transferred to the cold and spun down at different times (0-10-20-30 minutes). External Na+ concentrations were measured in the supernatents by atomic corption. A kinetic analysis of the inhibition of ouabain sensitive Na+ efflux as a function of different aminoglycoside concentrations was done and the $IC_{50}$ for each compound was calculated. The compounds of the formula I are effective in a concentration range from $10^{-9}$ to $10^{-6}$ M.

'In vivo' assays to test the hypotensive activities of aminoglycoside steroids of formula I Indirect measurements of systolic blood pressure was carried out in groups of 4 spontaneously hypertensive rats (SHR,Kyoto), 8 to 10 weeks of age, supplied by Charles Rives, Italy. The animals were maintained in an environment of 36° C. for 10 to 15 minutes to allow pulse pressure to be recorded and then systolic blood pressure and heart rate were measured by the indirect tail cuff method using a W+W, BP recorder, model 8005. The compounds were given orally, suspended in 5% arabic gum, once a day for 4 consecutive days and measurements were carried out before beginning the treatment and 1 and 5 hours after dosing in both the first and fourth day of treatment. Control animals received the vehicle only (0.2 ml/100 g body weight). Drug induced changes in systolic blood pressure were calculated as differences from the pretreatment values.

The formulation of the compounds of the invention as pharmaceutical composition may include solid formulations such as capsules, tablets and powders, or liquid formulations such as elixirs, syrups and suspensions for oral administration. Alternatively, the inventive compounds (I) may be formulated as injections or suppositories.

A carrier and diluent may be included in the pharmaceutical composition which is selected from pulverulent solid carriers such as lactose, saccharose, dextrose, mannitol, sorbitol, cellulose, and glycine etc.

The composition may further contain a lubricant, a binder or a disintegrator. Examples of suitable lubricants are silicon dioxide, talc, magnesium stearate and polyethylene glycol. Examples of suitable binders are starch, gelatin, tragacanth, methyl cellulose and polyvinyl pyrrolidone. Examples of suitable disintegrators are starch and agar etc.

The following Examples illustrate preferred embodiments of the invention.

EXAMPLE 1

3-[(3-amino-3-deoxy-β-D-glucopyranosyl)oxy]-14,21-dihydroxy-(3β,5β,14β,20R)-24-nor-cholanic acid 376 mg of 3,14,21-trihydroxy-(3β,5β,14β,20R)-24-nor-cholanic acid lactone were dissolved in 100 ml of anhydrous benzene, 3.4 g of Fetizon reagent were added, the mixture was brought to reflux and, with azeotropic distillation, a solution of 928 mg of 3-deoxy-2,4,6-tri-O-acetyl-3-trifluoroacetamido-α-D-glucopyranosyl bromide in 100 ml of anhydrous benzene was added dropwise over 3 hours. The mixture was cooled to r.t., filtered, the organic solution washed with a saturated sodium hydrogen carbonate solution, with a saturated sodium chloride solution, dried over sodium sulfate and evaporated to dryness. The crude residue was chromatographed on silica gel with cyclohexane-ethyl acetate 1:1 to afford 531 mg of 3-[(3- deoxy-2,4,6-tri-O-acetyl-3-trifluoroacetamido-α-D-glucopyranosyl)oxy]-14,21-dihydroxy-(3β,5β,14β,20R)-24-nor-cholanic acid lactone. 531 mg of the aforementioned protected glycoside were dissolved in 28 ml of 0.1 N potassium hydroxide in methanol-water 99:1. After 24 hours at r.t., the solution was evaporated to dryness, the residue dissolved in water and acidified at pH 5 by addition of acetic acid. The resulting precipitate was filtered, washed with water and dried to afford 300 mg of the title compound.

EXAMPLE 2

3-[(3-amino-3-deoxy-β-D-glucopyranosyl)ox)]-14,21-dihydroxy-(3β,5β,14β,2OR)-24-nor-cholanic acid lactone 540 mg of 3-[(3-amino-3-deoxy-β-D-glucopyranosyl)oxy]-14,21-dihydroxy-(3β,5β,14β,20R)-24-nor-cholanic acid were suspended in 150 ml of distilled water and brought into solution acidifying at pH 1 with 1 N hydrochloric acid. After 1 hour at r.t. the solution was brought at pH 8 with a saturated sodium hydrogen carbonate solution, extracted with chloroform-methanol 8:2, the organic layer washed with a saturated sodium chloride solution, dried over sodium sulfate, evaporated to dryness and crystallized from absolute ethyl alcohol to afford 430 mg of the title compound, m.p. 278°–282° C.

EXAMPLE 3

3-[(3-amino-3-deoxy-β-D-glucopyranosyl)oxy]-14,21-dihydroxy-(3β,5β,14β,2OS)-24-nor-cholanic acid Operating as in Example 1 but employing 3,14,21-trihydroxy-(3β, 5β,14β,2OS)-24-nor-cholanic acid lactone, the title compound was obtained in 58% yield.

EXAMPLE 4

3-[(3-amino-3-deoxy-β-D-glucopyranosyl)oxy]-14,21-dihydroxy-(3β,5β,14β,2OS)-24-nor-cholanic acid lactone Operating as in Example 2 but employing 3-[(3-amino-3-deoxy-β-D-glucopyranosyl)oxy]-14,2-dihydroxy-(3β,5β, 14β,2OS)-24-nor-cholanic acid, the title compound was obtained in 78% yield.

EXAMPLE 5

3-[(3-amino-3-deoxy-β-D-glucopyranosyl)oxy]-21-hydroxy-(3β,5β,20R)-Δ14-24-nor-cholenic acid Operating as in Example 1 but employing 3,21-dihydroxy-3β,5β,20R)-Δ-14-24-nor-cholenic acid lactone, the title compound was obtained in 72% yield.

EXAMPLE 6

3-[(3-amino-3-deoxy-β-D-glucopyranosyl)oxy]-21-hydroxy-(3,5,2OR)-Δ14-24-nor-cholenic acid lactone Operating as in Example 2 but employing 3-[(3-amino-3-deoxy-β-D-glucopyranosyl)oxy]-21-hydroxy-(3β,5β, 2OR)-Δ14-24-nor-cholenic acid, the title compound was obtained in 90% yield, m.p. 188°–190° C.

EXAMPLE 7

3-[(3-amino-3-deoxy-β-D-glucopyranosyl)oxy]-21-hydroxy-(3β,5β,2OS)-Δ14-24-nor-cholenic acid Operating as in Example 1 but employing 3,21-dihydroxy-(3β,5β,2OS)-Δ14-24-nor-cholenic acid lactone, the title compound was obtained in 69% yield.

EXAMPLE 8

3-[-(3-amino-3-deoxy-β-D-glucopyranosyl)oxy]-21-hydroxy-(3β,5β,20S)-Δ14-24-nor-cholenic acid lactone Operating as in Example 2 but employing 3-[(3-amino-3-deoxy-β-D-glucopyranosyl)oxy]-21-hydroxy-(3β,5β,20S)-Δ14-24-nor-cholenic acid, the title compound was obtained in 79% yield, m.p. 190°–192° C.

EXAMPLE 9

3-[(2-amino-2-deoxy-β-D-glucopyranosyl)oxy]-14,21-dihydroxy-(3β,5β,14β,2OR)-24-nor-cholanic acid Operating as in Example 1 but employing 2-deoxy-3,4,6-tri-O-acetyl-2-trifluoroacetamido-α-D-glucopyranosyl bromide, the title compound was obtained in 52% yield.

EXAMPLE 10

3-[-(2-amino-2-deoxy-β-D-qlucopyranosyl)oxy]-14,21-dihydroxy-(3β,5β,14β,2OR)-24-nor-cholanic acid lactone Operating as in Example 2 but employing 3-(-2-amino-2-deoxy-β-D-glucopyranosyl)oxy]-14,21-dihydroxy-(3β,5β, 14β,2OR)-24-nor-cholanic acid, the title compound was obtained in 78% yield.

EXAMPLE 11

3-[(3-amino-2,3,6-trideoxy-α-L-lyxo-hexopyranosyl)oxy]-14,21-dihydroxy-(3β,5β,14β,2OR)-24-nor-cholanic acid Operating as in Example 1 but employing 2,3,6-trideoxy-3-trifluoroacetamido-4-O-trifluoroacetyl-α-L-lyxo-hexopyranosyl chloride, the title compound was obtained in 63% yield.

EXAMPLE 12

3-[(3-amino-2,3,6-trideoxy-α-L-lyxo-hexopyranosyl)oxy]-14,21-dihydroxy-(3β,5β,14β,2OR)-24-nor-cholanic acid lactone Operating as in Example 2 but employing 3-[(3-amino-2,3,6-trideoxy-α-L-lyxo-hexopyranosyl)oxy]-14,21-dihydroxy-(3β, 5β,14β,2OR)-24-nor-cholanic acid, the title compound was obtained in 75% yield.

EXAMPLE 13

3-[(3-amino-2,3,6,trideoxy-α-L-lyxo-hexopyranosyl)oxy]-14,21-dihydroxy-(3β,5β,14β,2OS)-24-nor-cholanic acid Operating as in Example 3 but employing 2,3,6-trideoxy-3-trifluoroacetamido-4-O-trifluoroacetyl-α-lyxo-hexopy ranosyl chloride, the title compound was obtained in 60% yield.

EXAMPLE 14

3-[(3-amino-2,3,6-trideoxy-α-L-lyxo-hexopyranosyl)oxy]-14,21-dihydroxy-(3β,5β,14β,2OS)-24-nor-cholanic acid lactone Operating as in Example 2 but employing 3-[(3-amino-2,3,6-trideoxy-α-L-lyxo-hexopyranosyl)oxy]-14,21-dihydroxy-(3β,5β,14β,2OS)-24-nor-cholanic acid, the title compound was obtained in 74% yield.

EXAMPLE 15

3-[(3-amino-2,3,6-trideoxy-α-L-lyxo-hexopyranosyl)oxy]-21-hydroxy-(3β,5β,2OR)-Δ$^{14}$-24-nor-cholenic acid Operating as in Example 5 but employing 2,3,6-trideoxy-3-trifluoroacetamido-4-O-trifluoroacetyl-α-L-lyxo-hexopyranosyl chloride, the title compound was obtained in 70% yield.

EXAMPLE 16

3-[(3-amino-2,3,6-trideoxy-α-L-lyxo-hexopyranosyl)oxy]-21-hydroxy-(3β,5β,2OR)-Δ$^{14}$-24-nor-cholenic acid lactone Operating as in Example 2 but employing 3-[(3-amino-2,3,6-trideoxy-α-L-lyxo-hexopyranosyl)oxy]-21-hydroxy-(3β,5β, 2OR)-Δ$^{14}$-24-nor-cholenic acid, the title compound was obtained in 80% yield, m.p. 182°–186° C.

EXAMPLE 17

3-[(3-amino-2,3,6-trideoxy-α-L-lyxo-hexopyranosyl)oxy]-21-hydroxy-(3β,5β,2OS)-Δ$^{14}$-24-nor-cholenic acid Operating as in Example 7 but employing 2,3,6-trideoxy-3-tri-fluoroacetamido-4-O-trifluoroacetyl-α-L-lyxo-hexopyranosyl chloride, a mixture of α and β-glycosides was obtained in 70% yield.

By crystallization, the title compound was obtained in 40% yield, m.p. 161°–163° C.

EXAMPLE 18

3-[(3-amino-2,3,6-trideoxy-α-L-lyxo-hexopyranosyl)oxy-]-21-hydroxy-(3β,5β,2OS)-Δ$^{14}$-24-nor-cholenic acid lactone Operating as in Example 2 but employing 3-[(3-amino-2,3,6-trideoxy-α-L-lyxo-hexopyranosyl)oxy]-21-hydroxy-(3β,5β,2OS)-Δ$^{14}$-24-nor-cholenic acid, the title compound was obtained in 75% yield, m.p. 220°–224° C.

EXAMPLE 19

3-[(3-amino-2,3,6-trideoxy-β-L-lyxo-hexopyranosyl)oxy]-21-hydroxy-(3β,5β,2OS)-Δ$^{14}$-nor-cholenic acid The residue of the mother liquors obtained in Example 17 was crystallized giving the title compound in 25% yield.

EXAMPLE 20

3-[(3-amino-2,3,6-trideoxy-β-L-lyxo-hexopyranosyl)oxy]-21-hydroxy-(3β,5β,2OS)-Δ$^{14}$-nor-cholenic acid lactone Operating as in Example 2 but employing 3-[(3-amino-2,3,6-trideoxy-α-L-lyxo-hexopyranosyl)oxy]-21-hydroxy-(3β,5β, 2OS)-Δ$^{14}$-24-nor-cholenic acid, the title compound was obtained in 76% yield.

EXAMPLE 21

3-[(3-amino-3,6-dideoxy-α-L-mannopyranosyl)oxy]-14,21-dihydroxy-(3β,5β,14β,2OR)-24-nor-cholanic acid Operating as in Example 1 but employing 2,4-di-O-acetyl-3,6-dideoxy-3-trifluoroacetamido-α-L-mannopyranosyl bromide, the title compound was obtained in 75% yield.

EXAMPLE 22

3-[(3-amino 3,6-dideoxy-α-L-mannopyranosyl)oxy]-14,21-dihydroxy-(3β,5β,14β, 2OR)-24-nor-cholanic acid lactone Operating as in Example 2 but employing 3-[(3-amino-3,6-dideoxy-α-L-mannopyranosyl)oxy]-14,21-dihydroxy-(3β,5β,14β, 2OR)-24-nor-cholanic acid, the title compound was obtained in 80% yield.

EXAMPLE 23

3-[(3-amino-3,6-dideoxy-α-L-mannopyranosyl oxy]-14,21-dihydroxy-(3β,5β,14β,2OS)-24-nor-cholanic acid lactone Operating as in Example 3 but employing 2,4-di-O-acetyl-3,6-dideoxy-3-trifluoroacetamido-α-L-mannopyranosyl bromide, the title compound was obtained in 60% yield.

EXAMPLE 24

3-[(3-amino-3,6-dideoxy-α-L-mannopyranosyl)oxy]-14,21-dihydroxy-(3β,5β,14β,2OS)-24-nor-cholanic acid lactone Operating as in Example 2 but employing 3- (3-amino-3,6-dideoxy-α-L-mannopyranosyl)oxy]-14,21-dihydroxy-(3β,5β,14β,2OS)-24-nor-cholanic acid, the title compound was obtained in 95% yield.

EXAMPLE 25

3-[(3-amino-3,6-dideoxy-α-L-mannopyranosyl)oxy]-21-(3β,5β,2OR)-Δ$^{14}$-24-nor-cholenic acid Operating as in Example 5 but employing 2,4-di-O-acetyl-3,6-dideoxy-3-trifluoroacetamido-α-L-mannopyranosyl bromide, the title compound was obtained in 60% yield.

EXAMPLE 26

3-[(3-amino-3,6-dideoxy-α-L-mannopyranosyl)oxy]-21-hydroxy(3β,5β,2OR)-Δ$^{14}$-24-nor-cholenic acid lactone Operating as in Example 2 but employing 3-(3-amino-3,6- -dideoxy-α-L-mannopyranosyl)oxy]-21-hydroxy-(3β,5β, 2OR)-Δ$^{14}$-24-nor-cholenic acid, the title compound was obtained in 80% yield.

EXAMPLE 27

3-[(3-amino-3,6-dideoxy-α-L-mannopyranosyl)oxy]-21-hydroxy-(3β,5β,2OS)-Δ$^{14}$-24-nor-cholenic acid Operating as in Example 7, but employing 2,4-di-O-acetyl-3,6-dideoxy-3-trifluoroacetamido-α-L-mannopyranosyl bromide, the title compound was obtained in 66% yield.

EXAMPLE 28

3-[(3-amino-3,6-dideoxy-α-L-mannopyranosyl)-oxy]-21-(3β,5β,2OS)-Δ$^{14}$-24-nor-cholenic acid lactone Operating as in Example 2, but employing 3-[(3-amino-3,6-dideoxy-α-L-mannopyranosyl)oxy]-21-hydroxy-(3β,5β, 2OS)-Δ$^{14}$-24-nor-cholenic acid, the title compound was obtained in 74% yield.

EXAMPLE 29

3-[(3-amino-3,6-dideoxy-α-D-altropyranosyl)oxy]-14,21-dihydroxy-(3β,5β,14β,2OR)-24-nor-cholanic acid Operating as in Example 1, but employing 3,6-dideoxy-2,4-di-O-acetyl-3-trifluoroacetamido-α-D-altropyranosyl bromide, the title compound was obtained in 70% yield.

EXAMPLE 30

3-[(3-amino-3,6-dideoxy-α-D-altropyranosyl)oxy]-14,21-dihydroxy-(3β,5β,14β,2OR)-24-nor-cholanic acid lactone Operating as in Example 2, but employing 3-[(3-amino-3,6-dideoxy-α-D-altropyranosyl)oxy]-14,21-dihydroxy-(3β,5β, 14β,2OR)-24-nor-cholanic acid, the title compound was obtained in 75% yield.

EXAMPLE 31

3-[(3-amino-3,6-dideoxy-α-D-altropyranosyl)oxy-14,21-dihydroxy-(3β,5β,14β,2OS)-24-nor-cholanic acid Operating as in Example 3, but employing 3,6-dideoxy-2,4-di-O-acetyl-3-trifluoroacetamido-α-D-altropyranoyl bromide, the title compound was obtained in 55% yield.

EXAMPLE 32

3-[(3-amino-3,6-dideoxy-α-D-altropyranosyl)oxy]-14,21-dihydroxy-(3β,5β,14β,2OS)-24-nor-cholanic acid lactone Operating as in Example 2, but employing 3-[(3-amino-3,6-dideoxy-α-D-altropyranosyl)oxy]-14,21-dihydroxy-(3β,5β, 14β,2OS)-24-nor-cholanic acid, the title compound was obtained in 73% yield.

EXAMPLE 33

3-[(3-amino-3,6-dideoxy-α-D-altropyranosyl)oxy]-21-hydroxy(3β,5β,14β2OR)-Δ$^{14}$-24-nor-cholenic acid Operating as in Example 5, but employing 3,6-dideoxy-2,4-di-O-acetyl-3-trifluoroacetamido-α-D-altropyranosyl bromide, the title compound was obtained in 75% yield.

EXAMPLE 34

3-[(3-amino-3,6-dideoxy-α-D-altropyranosyl)oxy]-21-hydroxy-(3β,5β, 2OR)-Δ$^{14}$-24-nor-cholenic acid lactone Operating as in Example 2, but employing 3-[(3-amino-3,6-dideoxy-α-D-altropyranosyl)oxy]-21-hydroxy-(3β,5β,14β, 2OR)-Δ$^{14}$-24-nor-cholenic acid, the title compound was obtained in 77% yield.

EXAMPLE 35

3-[(3-amino-3,6-dideoxy-α-D-altropyranosyl)oxy]-21-hydroxy-(3β,5β, 2OS)-Δ$^{14}$-24-nor-cholenic acid Operating as in Example 7, but employing 3,6-dideoxy-2,4-O-di-acetyl-3-trifluoroacetamido-α-D-altropyranosyl bromide, the title compound was obtained in 80% yield.

EXAMPLE 36

3-[3-amino-3,6-dideoxy-α-D-altropyranosyl)oxy]-21-hydroxy-(3β,5β, 2OS)-Δ$^{14}$-24-nor-cholenic acid lactone Operating as in Example 2, but employing 3-[(3-amino-3,6-di-deoxy-α-D-altropyranosyl)oxy]-21-hydroxy-(3β,5β,14β, 2OS)-Δ$^{14}$-24-nor-cholenic acid, the title compound was obtained in 73% yield.

EXAMPLE 37

3-[(3,6-dideoxy-3-dimethylamino-α-D-altropyranosyl)oxy]-14,21-dihydroxy-(3β,5β,14β,2OR)-24-nor-cholanic acid Operating as in Example 1, but employing 3,6-dideoxy-2,4-di-O-acetyl-3-dimethylamino-α-D-altropyranosyl bromide hydrobromide, the title compound was obtained in 77% yield.

EXAMPLE 38

3-[(3,6-dideoxy-3-dimethylamino-α-D-altropyranosyl)oxy]-14,21-dihydroxy-(3β,5β,14β,2OR)-24-nor-cholanic acid lactone Operating as in Example 2, but employing 3-[(3,6-dideoxy-3-di-methylamino-α-D-altropyranosyl)oxy]-14,21-dihydroxy-(3β,5β,14β, 2OR)-24-nor-cholanic acid, the title compound was obtained in 80% yield.

EXAMPLE 39

3-[(3-amino-2,3,6-trideoxy-α-D-arabino-hexopyranosyl)oxy]-14,21-dihydroxy-(3β,5β,14β,2OR)-24-nor-cholanic acid Operating as in Example 1, but employing 2,3,6-trideoxy-3-tri-fluoroacetamido-4-O-trifluotoacetyl-α-D-arabino-hexopyranosyl chloride, a mixture of α and β-glycosides was obtained in 63% yield. The title compound was obtained by crystallization in 30% yield.

EXAMPLE 40

3-[(3-amino-2,3,6-trideoxy-α-D-arabino-hexopyranosyl)oxy]-14,21-dihydroxy-(3β,5β,14β,2OR)-24-nor-cholanic acid lactone Operating as in Example 2, but employing 3-[(3-amino-2,3,6-trideoxy-α-D-arabino-hexopyranosyl)oxy]-14,21-dihydroxy(3β,5β,14β,2OR)-24-nor-cholanic acid, the title compound was obtained in 67% yield.

EXAMPLE 41

3-(3-amino-2,3,6-trideoxy-β-D-arabino-hexopyranosyl)oxy]-14,21-dihydroxy-(3β,5β,14β,2OR)-24-nor-cholanic acid The residue of the mother liquors obtained in Example 39 was crystallized giving the title compound in 28% yield.

EXAMPLE 42

3-[(3-amino-2,3,6-trideoxy-β-D-arabino-hexopyranosyl)oxy]-14,21-dihydroxy-(3β,5β,14β,2OR)-24-nor-cholanic acid lactone Operating as in Example 2, but employing 3-[(3-amino-2,3,6-trideoxy-β-D-arabino-hexopyranosyl)oxy]-14,21-dihydroxy-(3β,5β,14β,2OR)-24-nor-cholanic acid, the title compound was obtained in 73% yield.

EXAMPLE 43

3-[(3-amino-2,3,6-trideoxy-α-D-arabino-hexopyranosyl)oxy]-14,21-dihydroxy-(3β,5β,14β,20S)-24-nor-cholanic acid Operating as in Example 3, but employing 2,3,6-trideoxy-3-trifluoroacetamido-4-O-trifluoroacetyl-α-D-arabino-hexopyranosyl chloride, the title compound was obtained in 55% yield.

EXAMPLE 44

3-[(3-amino-2,3,6-trideoxy-α-D-arabino-hexopyranosyl)oxy]-14,21-dihydroxy-(3β, 5β,14β,20S)-24-nor-cholanic acid lactone Operating as in Example 2, but employing 3-[(3-amino-2,3,6-trideoxy-α-D-arabino-hexopyranosyl)oxy]-14,21-dihydroxy-(3β, 5β,14β,20S)-24-nor-cholanic acid, the title compound was obtained in 78% yield.

EXAMPLE 45

3-[(3-amino-2,3,6-trideoxy-α-D-arabino-hexopyranosyl)oxy]-21-hydroxy-(3β,5β,20R)-Δ$^{14}$-24-nor-cholenic acid Operating as in Example 5, but employing 2,3,6-trideoxy-3-trifluoroacetamido-4-O-trifluoroacetyl-α-D-arabino-hexopyranosyl chloride, the title compound was obtained in 58% yield.

EXAMPLE 46

3-[(3-amino-2,3,6-trideoxy-α-D-arabino-hexopyranosyl)oxy]-21-hydroxy-(3β,5β,20R)-Δ$^{14}$-24-nor-cholenic acid lactone Operating as in Example 2, but employing 3-[(3-amino-2,3,6-trideoxy-α-D-arabino-hexopyranosyl)oxy]-21-hydroxy-(3β,5β, 20R)-Δ$^{14}$-24-nor-cholenic acid, the title compound was obtained in 75% yield.

EXAMPLE 47

3-[(3-amino-2,3,6-trideoxy-α-D-arabino-hexopyranosyl)oxy]-21-hydroxy-(3β,5β,20S)-Δ$^{14}$-24-nor-cholenic acid Operating as in Example 7, but employing 2,3,6-trideoxy-3-trifluoroacetamido-4-O-trifluoroacetyl-α-D-arabino-hexopyranosyl chloride, the title compound was obtained in 60% yield.

EXAMPLE 48

3-[(3-amino-2,3,6-trideoxy-α-D-arabino-hexopyranosyl)oxy]-21-hydroxy-(3β,5β,20S)-Δ$^{14}$-24-nor-cholenic acid lactone Operating as in Example 2, but employing 3-[(3-amino 2,3,6-trideoxy-α-D-arabino-hexopyranosyl)oxy]-21-hydroxy-(3β,5β, 20S)-Δ$^{14}$-24-nor-cholenic acid, the title compound was obtained in 75% yield.

EXAMPLE 49

3-[(2-amino-2-deoxy-β-D-glucopyranosyl)oxy]-21-hydroxy-(3β,5β,20S)-Δ$^{14}$-24-nor-cholenic acid Operating as in Example 7, but employing 2-deoxy-2-diphenyl-oxyphosphorylamino-3,4,6,-O-acetyl-2-D-glucopyranosyl bromide, the title compound was obtained in 55% yield.

EXAMPLE 50

3-[(2-amino-2-deoxy-β-D-glucopyranosyl)oxy]-21-hydroxy-(3β,5β,20S)-Δ$^{14}$-24-nor-cholenic acid lactone Operating as in Example 2, but employing 3-[(2-amino-2-deoxy-β-D-glucopyranosyl)oxy]-21-hydroxy-(3β,5β,20S)-Δ$^{14}$-24-nor-cholenic acid, the title compound was obtained in 70% yield, m.p. 192°–194° C.

EXAMPLE 51

3-[(3-amino-3,6-dideoxy-α-D-mannopyranosyl)oxy]-21-hydroxy-(3β,5β,20S)-Δ$^{14}$-24-nor-cholenic acid Operating as in Example 7, but employing 2,4-di-0-acetyl-3,6-dideoxy-3-trifluoroacetamido-α-D-mannopyranosylbromide, the title compound was obtained in 65% yield.

EXAMPLE 52

3-(3-amino-3,6-dideoxy-α-D-mannopyranosyl)oxy]-21-hydroxy-(3β,5β,20S)-Δ$^{14}$-24-nor-cholenic acid lactone Operating as in Example 2, but employing 3-[(3-amino-3,6-dideoxy-α-D-mannopyranosyl)oxy]-21-hydroxy-(3β,5β, 20S)-Δ$^{14}$-24-nor-cholenic acid, the title compound was obtained in 70% yield, m.p. 200°–202° C.

EXAMPLE 53

3-[(3-amino-3-deoxy-α-D-mannopyranosyl)oxy]-21-hydroxy-(3β,5β,20S)-Δ$^{14}$-24-nor-cholenic acid Operating as in Example 7, but employing 2,4,6-tri-O-acetil-3-deoxy-3-trifluoroacetamido-α-D-mannopyranosyl bromide, the title compound was obtained in 75% yield.

EXAMPLE 54

3-[(3-amino-3-deoxy-α-D-mannopyranosyl)oxy]-21-hydroxy-(3β,5β,20S)-Δ$^{14}$-24-nor-cholenic acid lactone Operating as in Example 2, but employing 3-[(3-amino-3-deoxy-α-D-mannopyranosyl)oxy]-21-hydroxy-(3β,5β, 20S)-Δ$^{14}$-nor-cholenic acid, the title compound was obtained in 85% yield, m.p. 251°–253° C.

EXAMPLE 55

3-[(3-amino-3-deoxy-α-D-mannopyranosyl)oxy]-21-hydroxy-(3β,5β,20R)-Δ$^{14}$-24-nor-cholenic acid Operating as in Example 5, but employing 2,4,6-tri-O-acetyl-3-deoxy-3-trifluoroacetamido-α-D-mannopyranosyl bromide, the title compound was obtained in 50% yield.

EXAMPLE 56

3-[(3-amino-3-deoxy-α-D-mannopyranosyl)oxy]-21-hydroxy-(3β,5β,20R)-Δ$^{14}$-24-nor-cholenic acid lactone Operating as in Example 2, but employing 3-[(3-amino-3-deoxy-α-D-mannopyranosyl)oxy]-21-hydroxy-( 3β,5β,20R)-Δ$^{14}$-24-nor-cholenic acid, the title compound was obtained in 70% yield, m.p. 230°–232° C.

EXAMPLE 57

3-[(3-amino-3,6-dideoxy-β-L-altropyranosyl)oxy]-21-hydroxy-(3β,5β,20S)-Δ$^{14}$-24-nor-cholenic acid Operating as in Example 7, but employing 3,6-dideoxy-2,4-O-di-acetyl-3-trifluoro-acetamido-α-L- altropyranosylbromide, the title compound was obtained in 75% yield.

EXAMPLE 58

3-[(3-amino-3,6-dideoxy-α-L-altropyranosyl)oxy]-21-hydroxy-(3β,5β,2OS)-Δ$^{14}$-24-nor-cholenic acid lactone Operating as in Example 2, but employing 3-[(3-amino-3,6-dideoxy-α-L-altropyranosyl)oxy]-21-hydroxy-(3β,5β,2OS)-Δ$^{14}$-24-nor-cholenic acid, the title compound was obtained in 72% yield, m.p. 192°–194° C.

EXAMPLE 59

3-[(3-amino-3,6-dideoxy-α-L-altropyranosyl)oxy]-21-hydroxy-(3β,5β,2OR)-Δ$^{14}$-24-nor-cholenic acid Operating as in Example 5, but employing 3,6-dideoxy-2,4-O-di-acetyl-3-trifluoroacetamido-α-L-altropyranosyl bromide the title compound was obtained in 65% yield.

EXAMPLE 60

3-[(3-amino-3,6-dideoxy-α-L-altropyranosyl)oxy]-21-hydroxy-(3β,5β,2OR)-Δ$^{14}$-24-nor-cholenic acid lactone Operating as in Example 2, but employing 3-[(3-amino-3,6-dideoxy-α-L-altropyranosyl)oxy]-21-hydroxy-(3β,5β,2OR)-Δ$^{14}$-24-nor-cholenic acid, the title compound was obtained in 83% yield, m.p. 152°–155° C.

EXAMPLE 61

3-[(3-amino-2,3,6-trideoxy-α-D-arabino-hexopyranosyl)oxy]-21-hydroxy-(3β,5β,2OS)-Δ$^{14}$-24-nor-cholenic acid Operating as in Example 7, but employing 2,3,6-trideoxy-3-trifluoroacetamido-4-O-trifluoroacetyl-α-D-arabino-hexopyranosyl chloride, the title compound was obtained in 62% yield.

EXAMPLE 62

3-[(3-amino-2,3,6-trideoxy-α-D-arabino-hexopyranosyl)oxy]-21-hydroxy-(3β,5β,2OS)-Δ$^{14}$-24-nor-cholenic acid lactone Operating as in Example 2, but employing 3-[(3-amino-2,3,6-trideoxy-α-D-arabino-hexopyranosyl)oxy]-21-hydroxy-(3β,5β,2OS)-Δ$^{14}$-24-nor-cholenic acid, the title compound was obtained in 72% yield, m.p. 222°–226° C.

EXAMPLE 63

3-[(3-amino-2,3,6-trideoxy-α-D-arabino-hexopyranosyl)oxy]-21-hydroxy-(3β,5β,2OS)-Δ$^{14}$-24-nor-cholenic acid lactone Operating as in Example 5, but employing 2,3,6-trideoxy-3-trifluoroacetamido-4-O-trifluoroacetyl-α-D-arabino-hexopyranosylchloride, the title compound was obtained in 68% yield.

EXAMPLE 64

3-[(3-amino-2,3,6-trideoxy-α-D-arabino-hexopyranosyl)-oxy[-21-hydroxy-(3β,5β,2OR)-Δ$^{14}$-nor-cholenic acid lactone Operating as in Example 2, but employing 3-[(3-amino-2,3,6-trideoxy-α-D-arabino-hexopyranosyl)-oxy]-21-hydroxy-(3β,5β,2OR)-Δ$^{14}$-24-nor-cholenic acid, the title compound was obtained in 78% yield, m.p. 192°–195° C.

The invention is illustrated further in the below formulation examples:

Formulation 1

| Ingredient | Part |
| --- | --- |
| compound of the formula (I) | 45 |
| starch | 10 |
| lactose | 45 |

The ingredients are mixed thoroughly, and tablets or capsules are formulated from the mixture.

Formulation 2

| Ingredient | Part |
| --- | --- |
| compound of the formula (I) | 10 |
| lactose | 75 |
| magnesium oxide (MgO > 96%) | 15 |

The above ingredients are mixed thoroughly, and powders or fine granules are formed from the mixture.

Formulation 3

| Ingredient | Part |
| --- | --- |
| compound of the formula (I) | 1 |
| surface active agent | 1 |
| physiological saline | 98 |

The above ingredients are mixed under warming, and dispensed under sterile conditions into ampoules for use as injections.

We claim:

1. A compound having the general formula I wherein either $R_1$ represents a hydroxy group or an alkoxy group having from 1 to 4 carbon atoms and $R_2$ represents a hydrogen atom or an alkyl group having from 1 to 4 carbon atoms, or $R_1$ and $R_2$ taken together represent a chemical bond; $R_3$ represents an aminodeoxy or aminodideoxy or aminotrideoxy sugar residue of the D or L series; and either $R_4$ represents a hydroxy group and $R_5$ represents a hydrogen atom; or R and $R_5$ taken together represent a chemical bond; or a pharmaceutically acceptable salt thereof.

2. A compound according to formula I wherein the sugar residue is alkyl substituted.

3. A compound according to claim 1 wherein said sugar residue is a 2-amino or 2-alkylamino-2-deoxyhexopyranosyl, 3-amino or 3-alkylamino-3-deoxy-hexopyranosyl, 3-amino or 3-alkylamino-3,6-dideoxy-hexopyranosyl, 3-amino or 3-alkylamino-2,3,6-trideoxyhexopyranosyl or 4-amino or 4-alkylamino-2,4,6-trideoxy-hexopyranosyl residue of the D or L series.

4. A compound according to claim 1 wherein $R_1$ represents hydroxy, methoxy, ethoxy, propoxy or butoxy group and $R_2$ represents methyl, ethyl, propyl or butyl group or hydrogen atom.

5. A pharmaceutical composition for use in the treatment of hypertension comprising an effective amount of a compound as claimed in claim 1 in admixture with a pharmaceutically acceptable diluent or carrier.

6. A process for treating hypertension in a patient comprising administering to a patient a compound as claimed in claim 1 in an amount effective to reduce hypertension.

* * * * *

UNITED STATES PATENT AND TRADEMARK OFFICE
CERTIFICATE OF CORRECTION

PATENT NO. : 4,895,836
DATED : January 23, 1990
INVENTOR(S) : LAURA CHIODINI et al It is certified that error appears in the above-identified patent and that said Letters Patent is hereby corrected as shown below:

Col. 2, line 47, change "sore" to --some--

Col. 3, line 13, correct spelling of "Jorgensen"

Col. 4, line 5, should read "atomic absorption"

Col. 5, Example 2, line 13, change "ox)" to --oxy]--

Col. 6, Example 10, line 21, should read "B-D-glucopyranosyl)"

Col. 6, Example 10, line 25, should read "3-[(2-"

Col. 8, Example 22, line 4, insert a hyphen (-) after [(3-amino

Col. 8, Example 23, line 16, delete word "lactone"

Col. 8, Example 24, line 28, should read "3-[(3-"

Col. 8, lines 34-35, should read "21-hydroxy--"

Col. 8, line 46, should read "3-[(3-amino-"

Col. 8, line 63, should read "21-hydroxy-"

Col. 9, line 29, correct spelling of "altropyranosyl"

Col. 9, line 44, delete "14B"

Col. 10, line 3, should read "3-[(3-"

Col. 10, line 53, should read "3-[(3-"

Col. 11, line 57, should read "amino-2, 3, 6,"

UNITED STATES PATENT AND TRADEMARK OFFICE
CERTIFICATE OF CORRECTION

PATENT NO.  :  4,895,836

DATED       :  January 23, 1990

INVENTOR(S) :  LAURA CHIODINI et al

It is certified that error appears in the above-identified patent and that said Letters Patent is hereby corrected as shown below:

Col. 12, line 20,  should read "3-[(3-"

Col. 13, line 64,  should read "oxy]-21-"

Claim 1, col. 14, line 60, change "R" to $--R_4--$.

Signed and Sealed this

Twenty-sixth Day of March, 1991

*Attest:*

HARRY F. MANBECK, JR.

*Attesting Officer*      *Commissioner of Patents and Trademarks*